United States Patent
Daniell et al.

(10) Patent No.: US 12,134,794 B2
(45) Date of Patent: Nov. 5, 2024

(54) FERMENTATIVE PRODUCTION OF β-KETOADIPATE FROM GASEOUS SUBSTRATES

(71) Applicant: LanzaTech, Inc., Skokie, IL (US)

(72) Inventors: James Daniell, Auckland (NZ); Michael Koepke, Skokie, IL (US); Rasmus Overgaard Jensen, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 17/241,792

(22) Filed: Apr. 27, 2021

(65) Prior Publication Data

US 2021/0340579 A1    Nov. 4, 2021

Related U.S. Application Data

(60) Provisional application No. 63/017,408, filed on Apr. 29, 2020.

(51) Int. Cl.
C12P 7/44     (2006.01)
C12N 1/20     (2006.01)

(52) U.S. Cl.
CPC ............... *C12P 7/44* (2013.01); *C12N 1/205* (2021.05); *C12Y 102/04002* (2013.01); *C12Y 103/01006* (2013.01); *C12Y 203/01019* (2013.01); *C12Y 207/02007* (2013.01); *C12Y 208/03006* (2013.01); *C12Y 301/0202* (2013.01); *C12Y 602/01005* (2013.01)

(58) Field of Classification Search
None
See application file for complete search history.

(56) References Cited

U.S. PATENT DOCUMENTS

| | | | |
|---|---|---|---|
| 7,972,824 B2 | 7/2011 | Simpson | |
| 8,293,509 B2 | 10/2012 | Simpson | |
| 8,658,408 B2 | 2/2014 | Simpson | |
| 8,900,836 B2 | 12/2014 | Simpson | |
| 9,068,202 B2 | 6/2015 | Tran | |
| 9,284,564 B2 | 3/2016 | Mueller | |
| 9,347,076 B2 | 5/2016 | Liew | |
| 9,359,611 B2 | 6/2016 | Koepke | |
| 9,410,130 B2 | 8/2016 | Koepke | |
| 9,738,875 B2 | 8/2017 | Koepke | |
| 9,890,384 B2 | 2/2018 | Mueller | |
| 9,957,531 B1 * | 5/2018 | Koepke | C12P 7/18 |
| 9,994,878 B2 * | 6/2018 | Koepke | C12P 7/52 |
| 10,174,303 B2 | 1/2019 | Behrendorff | |
| 10,316,337 B2 * | 6/2019 | Koepke | C12Y 301/0202 |
| 10,590,406 B2 | 3/2020 | Koepke | |
| 10,913,958 B2 | 2/2021 | Koepke | |
| 2011/0262975 A1 | 10/2011 | Berry | |
| 2012/0045807 A1 | 2/2012 | Simpson | |
| 2013/0157322 A1 | 6/2013 | Simpson | |
| 2015/0167028 A1 * | 6/2015 | Burgard | C12N 9/0006 435/254.2 |
| 2017/0159075 A1 * | 6/2017 | Osterhout | C12P 13/005 |
| 2018/0282481 A1 | 10/2018 | Beckham | |
| 2019/0185888 A1 | 6/2019 | Koepke | |
| 2021/0292732 A1 | 9/2021 | Liew | |

FOREIGN PATENT DOCUMENTS

| | | |
|---|---|---|
| CN | 102066551 A | 5/2011 |
| CN | 108884467 A | 11/2018 |
| JP | 2011515111 A | 5/2011 |
| JP | 2012000059 A | 1/2012 |
| WO | 2008028055 A2 | 3/2008 |
| WO | 2009064200 A2 | 5/2009 |
| WO | 2012015317 A1 | 2/2012 |
| WO | 2012177721 A1 | 12/2012 |
| WO | 2017066498 A1 | 4/2017 |
| WO | 2017099209 A1 | 6/2017 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
International Search Report and Written Opinion issued in corresponding International Application No. PCT/US2021/029421, dated Aug. 11, 2021, 14 pages.
Abrini, Arch Microbiol, 161: 345-351, 1994.
Drake, Acetogenic Prokaryotes, In: The Prokaryotes, 3rd edition, p. 354, New York, NY, 2006.
Kopke, Curr Opin Biotechnol, 22: 320-325, 2011.
Marcellin, Green Chem, 18: 3020-3028, 2016.
Perez, Biotechnol Bioeng, 110:1066-1077, 2012.
Ragsdale, Biochim Biophys Acta, 1784: 1873-1898, 2008.
Tanner, Int J System Bacteriol, 43: 232-236, 1993.
Johnson, C. W., 'Improving formate upgrading by Cupriavidus necator', DOE Bioenergy Technologies Office (BETO) 2019 Project Peer Review, 2019, p. 1-21. <URL: https://www.energy.gov/sites/default/files/2019/04/f61/Improving%20formate%20upgrading%20by%20Cupriavidus%20necator_NL0034713.pdf>.
Kupas et al., "Large scale analysis of protein-binding cavities using self-organizing maps and wavelet-based surface patches to describe functional properties, selectivity discrimination, and putative cross-reactivity" Proteins, Nov. 27, 2007, Wiley InterScience, pp. 1288-1306. DOI: 10.1002/prot.21823.
Partial Supplementary European Search Report issued in corresponding EP Application No. 21797586.1, dated May 22, 2024, 13 pages.

(Continued)

*Primary Examiner* — Christian L Fronda

(57) ABSTRACT

Provided herein are microorganisms and methods for fermentative production of β-ketoadipate from gaseous substrates such as carbon dioxide ($CO_2$), carbon monoxide (CO), and/or hydrogen ($H_2$). Additionally, the processes provided herein are methods for producing polymers containing β-ketoadipate, that can potentially enable a circular economy by diverting waste, e.g., plastic waste.

15 Claims, 1 Drawing Sheet

(56) References Cited

OTHER PUBLICATIONS

Extended European Search Report issued in corresponding EP Application No. 21797586.1, dated Aug. 12, 2024, 10 pages.
Skoog et al., "Biobased adipic acid-The challenge of developing the production host", Biotechnology Advances, Oct. 2018, pp. 2248-2263.

* cited by examiner

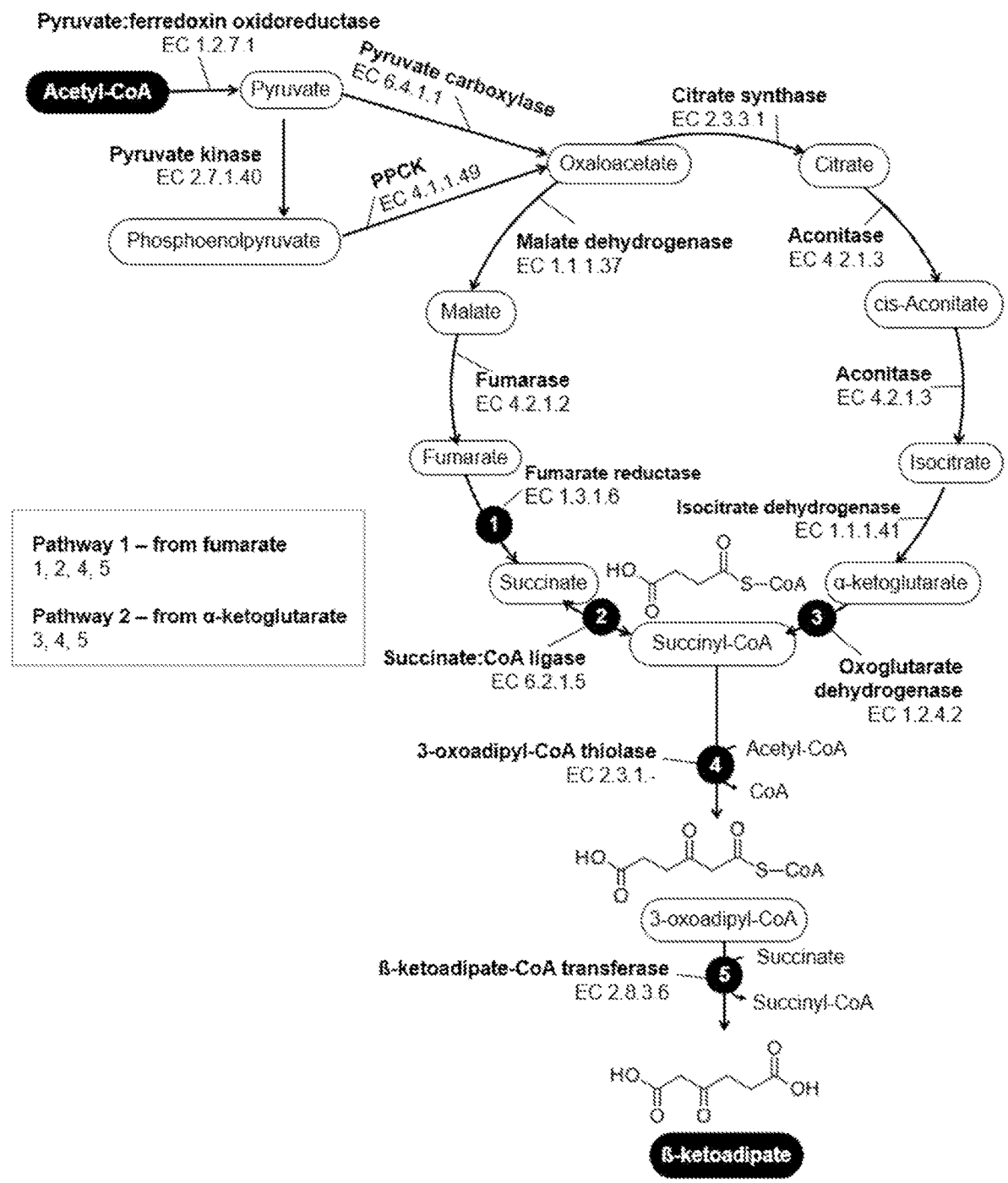

FERMENTATIVE PRODUCTION OF β-KETOADIPATE FROM GASEOUS SUBSTRATES

CROSS REFERENCE TO RELATED APPLICATIONS

This application claims the benefit of U.S. Provisional Patent Application No. 63/017,408 filed Apr. 29, 2020, the entirety of which is incorporated herein by reference.

FIELD

Provided are microorganisms and methods for the fermentative production of β-ketoadipate from gaseous substrates such as carbon dioxide ($CO_2$), carbon monoxide (CO), and/or hydrogen ($H_2$).

BACKGROUND

Mitigation of impending climate change requires drastic reductions in emissions of greenhouse gases (GHGs), such as those generated through the burning of fossil fuels like coal and oil. Although sustainable sources of fuels and chemicals are currently insufficient to significantly displace our dependence on fossil carbon, gas fermentation has recently emerged as an alternative platform for the biological fixation of such gases such as CO, $CO_2$, and/or $H_2$ into sustainable fuels and chemicals. In particular, gas fermentation technology can utilize a wide range of feedstocks including gasified carbonaceous matter (e.g., municipal solid waste or agricultural waste) or industrial waste gases (e.g., from steel mills or oil refineries) to produce ethanol, jet fuel, and a variety of other products. Gas fermentation alone could displace 30% of crude oil use and reduce global $CO_2$ emissions by 10%, but, as with any disruptive technology, many technical challenges must be overcome before this potential is fully achieved.

BRIEF DESCRIPTION OF THE DRAWINGS

The FIGURE is a diagram showing enzymatic pathways for the production of β-ketoadipate.

DETAILED DESCRIPTION

Provided is a microorganism for the production of β-ketoadipate, which comprises a heterologous enzyme that converts succinyl-CoA to 3-oxoadipyl-CoA and a heterologous enzyme that converts 3-oxoadipyl-CoA to β-ketoadipate. In one embodiment, the enzyme that converts succinyl-CoA to 3-oxoadipyl-CoA is 3-oxoadipyl-CoA thiolase (EC 2.3.1.-). In one embodiment, the enzyme that converts 3-oxoadipyl-CoA to 0-ketoadipate is β-ketoadipate-CoA transferase (EC 2.8.3.6). In one embodiment, the enzyme that converts 3-oxoadipyl-CoA to β-ketoadipate is thioesterase (EC 3.1.2.20). In one embodiment, the enzyme that converts 3-oxoadipyl-CoA to β-ketoadipate is phosphate butyryltransferase (Ptb) (EC 2.3.1.19) and butyrate kinase (Buk) (EC 2.7.2.7). Ptb and Buk are enzymes work together to convert acyl-CoAs and enoyl-CoAs to their corresponding acids or alkenates, respectively, while simultaneously generating ATP via substrate level phosphorylation, as described in WO 2017/0066498.

The succinyl-CoA may be produced via any native or heterologous pathway.

In one instance, the microorganism contains native enzymes that convert acetyl-CoA to fumarate, a native or heterologous enzyme that converts fumarate to succinate, and a native or heterologous enzyme that converts succinate to succinyl-CoA. In one embodiment, the enzyme that converts fumarate to succinate is fumarate reductase (EC 1.3.1.6). In one embodiment, the enzyme that converts succinate to succinyl-CoA is succinate:CoA ligase (EC 6.2.1.5).

In another instance, the microorganism contains native enzymes that convert acetyl-CoA to α-ketoglutarate and a native or heterologous enzyme that converts α-ketoglutarate to succinyl-CoA. In one embodiment, the enzyme that converts α-ketoglutarate to succinyl-CoA is oxoglutarate dehydrogenase (EC 1.2.4.2).

The conversion of 3-oxoadipyl-CoA to β-ketoadipate also yields a succinyl-CoA which can be fed back into the upstream step.

The microorganism may contain further genetic modifications, such as the knock out or knock down of genes to improve carbon flux to β-ketoadipate (e.g., to eliminate competing reactions that deplete intermediates), to overexpress key pathway enzymes, and/or to supplement or replace native enzymes with heterologous enzymes to improve pathway performance.

The β-ketoadipate may be enzymatically converted to additional downstream products as well. In one embodiment, the microorganism comprises a native or heterologous enzyme that converts β-ketoadipate to adipic acid.

The microorganism may be defined by a variety of structural and functional characteristics. In one embodiment, the microorganism is a C1-fixing microorganism. In one embodiment, the microorganism is a Wood-Ljungdahl microorganism. In one embodiment, the microorganism comprises a Wood-Ljungdahl pathway that converts CO, $CO_2$, and/or $H_2$ to acetyl-CoA. In one embodiment, the microorganism is a bacterium. In one embodiment, the microorganism is a member of a genus selected from *Acetobacterium, Alkalibaculum, Blautia, Butyribacterium, Clostridium, Eubacterium, Moorella, Oxobacter, Sporomusa,* and *Thermoanaerobacter.*

Also provided is a method of producing β-ketoadipate comprising culturing the microorganism in the presence of a gaseous substrate. Typically, the gaseous substrate comprises one or more of CO, $CO_2$, and $H_2$. In one embodiment, the gaseous substrate comprises syngas or industrial waste gas. For example, the syngas may be generated through gasification of waste plastic.

Further provided is a method of producing a polymer comprising culturing the microorganism of claim 1 in the presence of a gaseous substrate to produce β-ketoadipate and subsequently incorporating the β-ketoadipate into a polymer. In one embodiment, the polymer is β-ketoadipate-nylon.

Such polymers have the potential to displace existing petrochemical-derived polymers such as nylon 6,6. With applications ranging widely from textiles to auto parts, nylon 6,6 has a global market of $29 bn which is projected to grow by 6.5% by 2027. Traditionally, nylon 6,6 has been synthesized via polycondensation of adipic acid with hexamethylenediamine (HMDA), both of which are derived petrochemically. Not only does the conventional petrochemical process consume high energy and produce high GHG emissions, but the polymer produced by this process suffers from undesirable properties such as high water uptake/permeation and tendency to soften at moderate temperatures. Furthermore, other nylon replacements, such as nylon 6,10, have production routes that can result in toxic byproducts such as ricin.

β-ketoadipate-based polymers offer several distinct advantages over the conventional method to produce nylon 6,6, including i) an energy efficient route to convert gas feedstocks (e.g., gasified non-recyclable plastic waste) into high value polymers, ii) higher performance polymers due to the distinct chemical characteristics of beta-ketone functional group (which results in β-ketoadipate-nylon exhibiting 2-fold higher glass transition temperature and 1.5 fold higher melting temperature, along with lower water permeability compared to nylon 6,6), iii) ability to generate co-polymers that retain superior performance properties of β-ketoadipate without having to make a β-ketoadipate homopolymer, and finally, iv) option to polymerize β-ketoadipate via an industrially relevant salt polymerization process. In summary, this technology can potentially enable a circular economy by diverting waste, e.g., plastic waste, from oceans and landfills, and channeling that into production of new, infinitely recyclable materials.

DEFINITIONS

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility.

The terms "genetic modification," "genetic alteration," or "genetic engineering" broadly refer to manipulation of the genome or nucleic acids of a microorganism by humankind. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Wild type" refers to the typical form of an organism, strain, gene, or characteristic as it occurs in nature, as distinguished from mutant or variant forms.

"Native" or "endogenous" refers to a nucleic acid or protein that is present or expressed in the wild-type or parental microorganism from which the microorganism of the disclosure is derived. For example, an endogenous gene is a gene that is natively present in the wild-type or parental microorganism from which the microorganism of the disclosure is derived.

"Non-native" or "heterologous" refers to a nucleic acid or protein that is not present in the wild-type or parental microorganism from which the microorganism of the disclosure is derived. For example, a heterologous gene or enzyme may be derived from a different strain or species and introduced to or expressed in the microorganism of the disclosure. The heterologous gene or enzyme may be introduced to or expressed in the microorganism of the disclosure in the form in which it occurs in the different strain or species. Alternatively, the heterologous gene or enzyme may be modified in some way, e.g., by codon-optimizing it for expression in the microorganism of the disclosure or by engineering it to alter function, such as to reverse the direction of enzyme activity or to alter substrate specificity.

"Mutated" refers to a nucleic acid or protein that has been modified in the microorganism of the disclosure compared to the wild-type or parental microorganism from which the microorganism of the disclosure is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be any mutation that reduces, prevents, or blocks the biosynthesis of a product produced by an enzyme. The disruptive mutation may be a knockout (KO) mutation. The disruption may also be a knockdown (KD) mutation that reduces, but does not entirely eliminate, the expression or activity of a gene, protein, or enzyme. While KOs are generally effective in increasing product yields, they sometimes come with the penalty of growth defects or genetic instabilities that outweigh the benefits, particularly for non-growth coupled products. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

"Overexpressed" refers to an increase in expression of a nucleic acid or protein in the microorganism compared to the wild-type or parental microorganism from which the microorganism of the disclosure is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The disclosure may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a microorganism of the disclosure using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In one embodiment, nucleic acids are delivered to the microorganism of the disclosure using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

A "microorganism" is a microscopic organism, especially a bacterium, archaeon, virus, or fungus. The microorganism of the disclosure is typically a bacterium. As used herein, recitation of "microorganism" should be taken to encompass "bacterium."

A "parental microorganism" is a microorganism used to generate a microorganism of the disclosure. The parental microorganism may be a naturally occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In one embodiment, the parental microorganism is *Clostridium autoethanogenum* LZ1561, which was deposited with Deutsche Sammlung von Mikroorganismen and Zellkulturen GmbH (DSMZ) located at Inhoffenstraße 7B, D-38124 Braunschweig, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism.

The microorganism of the disclosure may be further classified based on functional characteristics. For example, the microorganism of the disclosure may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/− [1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/− [2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoaceticum*) | + | + | + | + | − [3] | + | + |
| *Oxobacter pfennigii* | + | + | + | + | − | + | + |
| *Sporomusa ovata* | + | + | + | + | − | + | +/− [4] |
| *Sporomusa silvacetica* | + | + | + | + | − | + | +/− [5] |
| *Sporomusa sphaeroides* | + | + | + | + | − | + | +/− [6] |
| *Thermoanaerobacter kivui* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1 carbon source. Typically, the microorganism of the disclosure is a C1-fixing microorganism. In one embodiment, the microorganism of the disclosure is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the disclosure is an anaerobe. In one embodiment, the microorganism of the disclosure is derived from an anaerobe identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, Biochim Biophys Acta, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, NY, 2006). All naturally occurring acetogens are C1-fixing, anaerobic, autotrophic, and non-methanotrophic. Typically, the microorganism of the disclosure is an acetogen. In one embodiment, the microorganism of the disclosure is derived from an acetogen identified in Table 1.

An "ethanologen" is a microorganism that produces or is capable of producing ethanol. Typically, the microorganism of the disclosure is an ethanologen. In one embodiment, the microorganism of the disclosure is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the disclosure is an autotroph. In one embodiment, the microorganism of the disclosure is derived from an autotroph identified in Table 1.

A "carboxydotroph" is a microorganism capable of utilizing CO as a sole source of carbon and energy. Typically, the microorganism of the disclosure is a carboxydotroph. In one embodiment, the microorganism of the disclosure is derived from a carboxydotroph identified in Table 1.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

More broadly, the microorganism of the disclosure may be derived from any genus or species identified in Table 1. For example, the microorganism may be a member of a genus selected from the group consisting of *Acetobacterium, Alkalibaculum, Blautia, Butyribacterium, Clostridium, Eubacterium, Moorella, Oxobacter, Sporomusa,* and *Thermoanaerobacter*. In particular, the microorganism may be derived from a parental bacterium selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kivui*.

In one embodiment, the microorganism of the disclosure is derived from the cluster of Clostridia comprising the species *Clostridium autoethanogenum, Clostridium ljungdahlii,* and *Clostridium ragsdalei*. These species were first reported and characterized by Abrini, Arch Microbiol, 161: 345-351, 1994 (*Clostridium autoethanogenum*), Tanner, Int J System Bacteriol, 43: 232-236, 1993 (*Clostridium ljungdahlii*), and Huhnke, WO 2008/028055 (*Clostridium ragsdalei*).

These three species have many similarities. In particular, these species are all C1 fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, Biotechnol Bioeng, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Kopke, Curr Opin Biotechnol, 22: 320-325, 2011).

Thus, in summary, many of the characteristics of *Clostridium autoethanogenum, Clostridium ljungdahlii,* or *Clostridium ragsdalei* are not specific to that species, but are rather general characteristics for this cluster of C1 fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

"Substrate" refers to a carbon and/or energy source for the microorganism of the disclosure. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the disclosure typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

In certain embodiments, the fermentation is performed in the absence of carbohydrate substrates, such as sugar, starch, lignin, cellulose, or hemicellulose.

The microorganism of the disclosure may be cultured to produce one or more products. For instance, the microorganism of the disclosure may produce or may be engineered to produce ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and monoethylene glycol (WO 2019/126400). In certain embodiments, microbial biomass itself may be considered a product. These products may be further converted to produce at least one component of diesel, jet fuel, and/or gasoline. Additionally, the microbial biomass may be further processed to produce a single cell protein (SCP).

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism but is not produced by a genetically unmodified microorganism from which the genetically modified microorganism is derived. For example, β-ketoadipate is a non-native product of *Clostridium autoethanogenum*, *Clostridium ljungdahlii*, and *Clostridium ragsdalei*.

Genetic engineering of microorganisms, such as Clostridia, can tremendously expand their ability to produce many important fuel and chemical molecules other than native products, such as ethanol. However, until recently, Clostridia were considered genetically intractable and therefore generally off limits to extensive metabolic engineering efforts. In recent years several different methods for genome engineering for Clostridia have been developed including intron-based methods (ClosTron), allelic exchange methods (ACE), Triple Cross, methods mediated through I-SceI, MazF, and other methods such as Cre-Lox and CRISPR/Cas9. However, it remains extremely challenging to iteratively introduce more than a few genetic changes, due to slow and laborious cycling times and limitations on the transferability of these genetic techniques across species. Furthermore, we do not yet sufficiently understand C1 metabolism in Clostridia to reliably predict modifications that will maximize C1 uptake, conversion, and carbon/energy/redox flows towards product synthesis. Accordingly, introduction of target pathways in Clostridia remains a tedious and time-consuming process.

Reference to a salt (e.g., β-ketoadipate or acetate) should be taken to also include the corresponding acid (e.g., β-ketoadipic acid or acetic acid). β-ketoadipate may also be referred to as 3-oxoadipate.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product account for at least about 5%, 10%, 15%, 20%, 30%, 50%, or 75% of all fermentation products produced by the microorganism of the disclosure. In one embodiment, the target product accounts for at least 10% of all fermentation products produced by the microorganism of the disclosure, such that the microorganism of the disclosure has a selectivity for the target product of at least 10%. In another embodiment, the target product accounts for at least 30% of all fermentation products produced by the microorganism of the disclosure, such that the microorganism of the disclosure has a selectivity for the target product of at least 30%.

The term "fermentation" should be interpreted as a metabolic process that produces chemical changes in a substrate. For example, a fermentation process receives one or more substrates and produces one or more products through utilization of one or more microorganisms. The term "fermentation," "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous". "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

Typically, the fermentation is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition.

One embodiment is a microorganism comprising a heterologous enzyme that converts succinyl-CoA to 3-oxoadipyl-CoA and a heterologous enzyme that converts 3-oxoadipyl-CoA to β-ketoadipate.

The microorganism of an embodiment, wherein the enzyme that converts succinyl-CoA to 3-oxoadipyl-CoA is 3-oxoadipyl-CoA thiolase (EC 2.3.1.-).

The microorganism of an embodiment, wherein the enzyme that converts succinyl-CoA to 3-oxoadipyl-CoA is 3-oxoadipyl-CoA thiolase (EC 2.3.1.-).

The microorganism of an embodiment, wherein the enzyme that converts 3-oxoadipyl-CoA to β-ketoadipate is thioesterase (EC 3.1.2.20).

The microorganism of an embodiment, wherein the enzyme that converts 3-oxoadipyl-CoA to β-ketoadipate is phosphate butyryltransferase (EC 2.3.1.19) and butyrate kinase (EC 2.7.2.7).

The microorganism of an embodiment, wherein the microorganism further comprises a native or heterologous enzyme that converts fumarate to succinate.

The microorganism of an embodiment, wherein the enzyme that converts fumarate to succinate is fumarate reductase (EC 1.3.1.6).

The microorganism of an embodiment, wherein the microorganism further comprises a native or heterologous enzyme that converts succinate to succinyl-CoA.

The microorganism of an embodiment, wherein the enzyme that converts succinate to succinyl-CoA is succinate:CoA ligase (EC 6.2.1.5).

The microorganism of an embodiment, wherein the microorganism further comprises native enzymes that convert acetyl-CoA to fumarate.

The microorganism of an embodiment, wherein the microorganism further comprises a native or heterologous enzyme that converts α-ketoglutarate to succinyl-CoA.

The microorganism of an embodiment, wherein the enzyme that converts α-ketoglutarate to succinyl-CoA is oxoglutarate dehydrogenase (EC 1.2.4.2).

The microorganism of an embodiment, wherein the microorganism further comprises native enzymes that convert acetyl-CoA to α-ketoglutarate.

The microorganism of an embodiment, wherein the microorganism further comprises a native or heterologous enzyme that converts β-ketoadipate to adipic acid.

The microorganism of an embodiment, wherein the microorganism is a C1-fixing microorganism.

The microorganism of an embodiment, wherein the microorganism is a Wood-Ljungdahl microorganism.

The microorganism of an embodiment, wherein the microorganism comprises a Wood-Ljungdahl pathway that converts CO, $CO_2$, and/or $H_2$ to acetyl-CoA.

The microorganism of an embodiment, wherein the microorganism is a bacterium.

The microorganism of an embodiment, wherein the microorganism is a member of a genus selected from *Acetobacterium, Alkalibaculum, Blautia, Butyribacterium, Clostridium, Eubacterium, Moorella, Oxobacter, Sporomusa,* and *Thermoanaerobacter*.

One embodiment is a method of producing β-ketoadipate comprising culturing the microorganism of claim 1 in the presence of a gaseous substrate.

The method of an embodiment, wherein the gaseous substrate comprises one or more of CO, $CO_2$, and $H_2$.

The method of an embodiment, wherein the gaseous substrate comprises syngas or industrial waste gas.

One embodiment is a method of producing a polymer comprising culturing the microorganism of claim 1 in the presence of a gaseous substrate to produce β-ketoadipate and subsequently incorporating the β-ketoadipate into a polymer.

The method of an embodiment, wherein the polymer is β-ketoadipate-nylon.

EXAMPLES

The following examples further illustrate the disclosure but, of course, should not be construed to limit its scope in any way.

Example 1

This example describes various combinations of heterologous and native enzymes for the production of β-ketoadipate from gaseous substrates. In particular, the microorganism may contain (the FIGURE):

a) a heterologous thiolase and a heterologous β-ketoadipate-CoA transferase;
b) a heterologous thiolase and a heterologous thioesterase;
c) a heterologous thiolase, a heterologous phosphate butyryltransferase, and a heterologous butyrate kinase;
d) a native fumarate reductase, a native succinate:CoA ligase, a heterologous thiolase and a heterologous β-ketoadipate-CoA transferase;
e) a native fumarate reductase, a native succinate:CoA ligase, a heterologous thiolase and a heterologous thioesterase;
f) a native fumarate reductase, a native succinate:CoA ligase, a heterologous thiolase, a heterologous phosphate butyryltransferase, and a heterologous butyrate kinase;
g) a heterologous fumarate reductase, a native succinate:CoA ligase, a heterologous thiolase and a heterologous β-ketoadipate-CoA transferase;
h) a heterologous fumarate reductase, a native succinate:CoA ligase, a heterologous thiolase and a heterologous thioesterase;
i) a heterologous fumarate reductase, a native succinate:CoA ligase, a heterologous thiolase, a heterologous phosphate butyryltransferase, and a heterologous butyrate kinase;
j) a native fumarate reductase, a heterologous succinate:CoA ligase, a heterologous thiolase and a heterologous β-ketoadipate-CoA transferase;
k) a native fumarate reductase, a heterologous succinate:CoA ligase, a heterologous thiolase and a heterologous thioesterase;
l) a native fumarate reductase, a heterologous succinate:CoA ligase, a heterologous thiolase, a heterologous phosphate butyryltransferase, and a heterologous butyrate kinase;
m) a native oxoglutarate dehydrogenase, a heterologous thiolase and a heterologous β-ketoadipate-CoA transferase;
n) a native oxoglutarate dehydrogenase, a heterologous thiolase and a heterologous thioesterase;
o) a native oxoglutarate dehydrogenase, a heterologous thiolase, a heterologous phosphate butyryltransferase, and a heterologous butyrate kinase;
p) a heterologous oxoglutarate dehydrogenase, a heterologous thiolase and a heterologous β-ketoadipate-CoA transferase;
q) a heterologous oxoglutarate dehydrogenase, a heterologous thiolase and a heterologous thioesterase; or
r) a heterologous oxoglutarate dehydrogenase, a heterologous thiolase, a heterologous phosphate butyryltransferase, and a heterologous butyrate kinase.

Example 2

This example provides metabolic modeling data for the fermentative production of β-ketoadipate from gaseous substrates.

A genome-scale metabolic model of *Clostridium autoethanogenum* like the one described by Marcellin, Green Chem, 18: 3020-3028, 2016 was utilized. Heterologous genes and metabolic reactions were added to this wild-type *Clostridium autoethanogenum* model structure to represent the incorporation of the β-ketoadipate production pathways. Although the model used for the experimental work described herein is based on *Clostridium autoethanogenum*, the results can reasonably be expected to apply to other Wood-Ljungdahl microorganisms as well, given similarities in metabolism.

Flux variability analysis was carried out to determine the feasibility of producing β-ketoadipate during growth on CO gas. The *C. autoethanogenum* model successfully produced β-ketoadipate using pathways via both fumarate and α-ketoglutarate. Flux balance analysis indicates that high β-ketoadipate selectivity is possible with ethanol co-production. Simulations were carried out using cobrapy version 0.17.0 (doi:10.1186/1752-0509-7-74).

| | Predicted practical maximum selectivity during growth |
|---|---|
| Pathway 1 (from fumarate) | 0.430 kg β-ketoadipate/Nm³ CO reacted |
| Pathway 2 (from α-ketoglutarate) | 0.324 kg β-ketoadipate/Nm³ CO reacted |

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavor in any country.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A C1-fixing microorganism comprising a heterologous enzyme 3-oxoadipyl-CoA thiolase having EC number 2.3.1.- and a heterologous enzyme β-ketoadipate-CoA transferase having EC number 2.8.3.6.

2. The microorganism of claim 1, wherein the microorganism further comprises a native or heterologous enzyme fumarate reductase having EC number 1.3.1.6.

3. The microorganism of claim 2, wherein the microorganism further comprises a native or heterologous enzyme succinate:CoA ligase having an EC number 6.2.1.5.

4. The microorganism of claim 2, wherein the microorganism further comprises native enzymes pyruvate:ferredoxin oxidoreductase having EC number 1.2.7.1, pyruvate carboxylase having EC number 6.4.1.1, malate dehydrogenase having EC number 1.1.1.37, fumarase having EC number 4.2.1.2, pyruvate kinase having EC number 2.7.1.40, and PPCK having EC number 4.1.1.49.

5. The microorganism of claim 1, wherein the microorganism further comprises a native or heterologous enzyme oxoglutarate dehydrogenase having EC number 1.2.4.2.

6. The microorganism of claim 5, wherein the microorganism further comprises native enzymes pyruvate:ferredoxin oxidoreductase having EC number 1.2.7.1, pyruvate carboxylase having EC number 6.4.1.1, pyruvate kinase having EC number 2.7.1.40, and PPCK having EC number 4.1.1.49, citrate synthase having EC number 2.3.3.1, aconitase having EC number 4.2.1.3 and isocitrate dehydrogenase having EC number 1.1.1.41.

7. The microorganism of claim 1, wherein the microorganism further comprises β-ketoadipate converted to adipic acid.

8. The microorganism of claim 1, wherein the microorganism is a Wood-Ljungdahl microorganism.

9. The microorganism of claim 1, wherein the microorganism is a bacterium.

10. The microorganism of claim 1, wherein the microorganism is a member of a genus selected from *Acetobacterium, Alkalibaculum, Blautia, Butyribacterium, Clostridium, Eubacterium, Moorella, Oxobacter, Sporomusa,* and *Thermoanaerobacter.*

11. A method of producing β-ketoadipate comprising culturing the microorganism of claim 1 in the presence of a gaseous substrate.

12. The method of claim 10, wherein the gaseous substrate comprises one or more of CO, $CO_2$, and $H_2$.

13. The method of claim 10, wherein the gaseous substrate comprises syngas or industrial waste gas.

14. A method of producing a polymer comprising culturing the microorganism of claim 1 in the presence of a gaseous substrate to produce β-ketoadipate and subsequently incorporating the β-ketoadipate into a polymer.

15. The method of claim 13, wherein the polymer is β-ketoadipate-nylon.

* * * * *